United States Patent [19]

Ramsey

[11] 4,057,415
[45] Nov. 8, 1977

[54] NITROISOTHIAZOLYLUREAS AS HERBICIDES

[75] Inventor: Arthur Albert Ramsey, Middleport, N.Y.

[73] Assignee: FMC Corporation, Philadelphia, Pa.

[21] Appl. No.: 697,455

[22] Filed: June 18, 1976

[51] Int. Cl.² .................... C07D 275/02; A01N 9/12
[52] U.S. Cl. ................................. 71/90; 260/306.8 A
[58] Field of Search .................... 260/306.8 A; 71/90

[56] References Cited

U.S. PATENT DOCUMENTS 3,143,540  8/1964  Meen et al. ............... 260/306.8 A

OTHER PUBLICATIONS

Robba et al., *Annales Pharmaceutiques Francaises*, 22, 1964, No. 3, pp. 201–210.

*Primary Examiner*—R. Gallagher
*Attorney, Agent, or Firm*—Harrison H. Young, Jr.; Henry R. Ertelt

[57] ABSTRACT

A new class of herbicidal compounds consisting of 1-alkyl- and 1,1-dialkyl-3-(3-substituted-4-nitro-5-isothiazolyl)ureas in which the 3-substituent consists of alkyl, alkoxy, alkylamino, alkylthio, alkylsulfinyl, and alkylsulfonyl exhibits preemergence and postemergence herbicidal activity, controlling effectively the growth of a wide spectrum of grassy and broad-leaved plant species. The synthesis of a representative member of this class is described in detail, and its utility is exemplified.

4 Claims, No Drawings

NITROISOTHIAZOLYLUREAS AS HERBICIDES

This invention describes novel herbicidal compounds, new herbicidal compositions, and new methods for preventing and destroying undesired plant growth by postemergence and preemergence application of said new and useful herbicidal compositions to the locus where control is desired. Effective control of the growth of a variety of grassy and broad-leaved plant species is obtained. At herbicidally effective levels of application, some compounds of the invention show selectivity favorable to corn and related species. The herbicidal compositions may be applied and utilized by commonly accepted methods.

Herbicidal (5-isothiazolyl)urea compounds having a cyano, carboxamide or alkoxycarbonyl group in the 4-position are described in the patent literature. See, for example, Belgian Pat. No. 817,903 and published French application No. 2,132,191 for compounds in which the 3-substituent of the isothiazole ring is alkyl. Copending applications Ser. No. 697,449, Ser. No. 697,457 and Ser. No. 697,458, filed of even date herewith, describe (5-isothiazolyl)ureas in which the 3-substituent on the isothiazole ring is substituted amino, alkoxy, substituted thio, sulfinyl or sulfonyl. It has now been found that excellent herbicidal activity is obtained by having present on the 4-position, instead of the cyano, carboxamide or alkoxycarbonyl group, a nitro group. Thus in one aspect of the invention, novel herbicidal compounds contain an isothiazole ring having the following classes of substitutents: on the 5-position, a substituted urea or alkanoylamino group, on the 4-position, a nitro group; and on the 3-position, an alkyl, alkoxy, substituted amino, alkylthio, alkylsulfinyl, or alkylsulfonyl group.

One group of herbicidal compounds in accordance with this invention has the following structure (on which the numbering of the various positions of the isothiazole ring is also indicated):

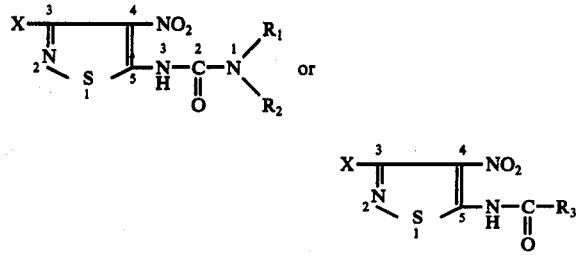

wherein
R$_1$ is alkyl, cycloalkyl or methoxy,
R$_2$ is alkyl or hydrogen, or R$_1$ and R$_2$ taken together from a divalent radical which may also contain a hetero atom,
R$_3$ is alkyl, alkenyl, haloalkyl or haloalkenyl,
X is an alkyl, alkoxy, alkylthio, alkylsulfinyl, alkylsulfonyl, alkylamino, dialkylamino or a cyclic alkyleneimino group.

the alkyl, cycloalkyl and alkenyl groups preferably have less than 10 carbon atoms. Examples of alkyl groups are methyl, ethyl, propyl, isopropyl, isobutyl, sec-butyl, tert-butyl, 2-pentyl, and so forth. The alkylene groups preferably contain a total of four or five catenated atoms, no more than one of which is oxygen, sulfur or nitrogen. In the most preferred compounds, R$_1$ and R$_3$ are lower alkyl and R$_2$ is H or methyl.

The compounds of this invention may be prepared, for example, by the following reaction sequences:

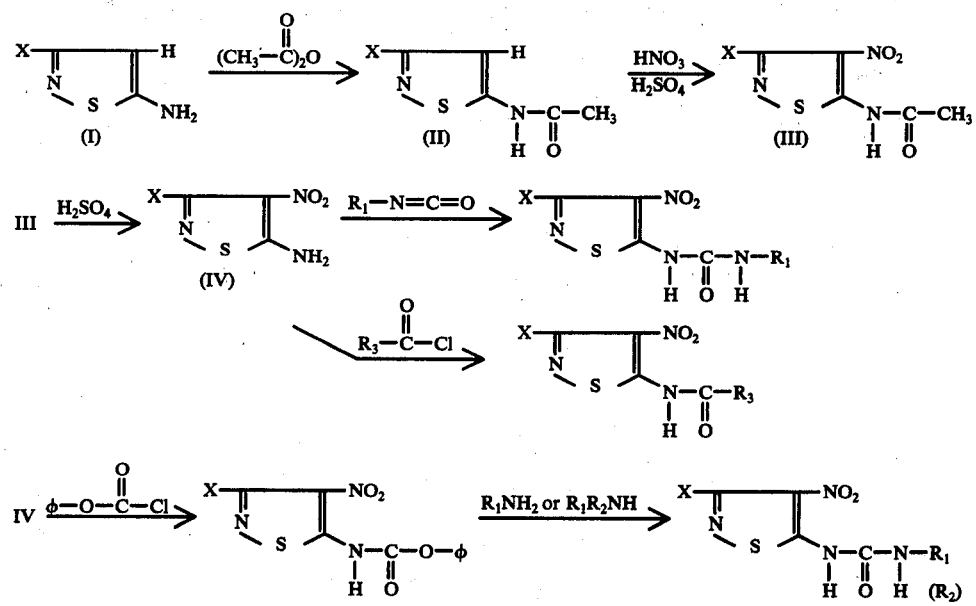

In the descriptions which follow, all temperatures are in degrees centigrade. All reduced pressures not otherwise designated are pressures normally attainable using a water aspirator.

EXAMPLE I

1-Methyl-3-(3-methyl-4-nitro-5-isothiazolyl)-urea

A mixture of 2.0 g of 5-amino-3-methyl-4-nitroisothiazole, 3.18 g of methyl isocyanate, and 0.59 ml of dibutyltin diacetate in 20 ml of dry tetrahydrofuran (dried with 5A molecular sieves) was heated under reflux for 18 hours. The mixture was cooled in an ice bath and the solid was isolated by filtration to give a solid, m.p. 234°–239°. The filtrate was allowed to evaporate leaving a solid, m.p. 231°–237°, which was slurried with methanol, filtered and dried to give a solid, m.p. 234°–239°. The solids were combined and recrystallized from methanol to give 2.2 g of yellow solid, m.p. 240°–243.5.°. Recrystallization of this solid from methanol did not change the melting point, but recrystallization from tetrahydrofuran-hexane increased the melting point to 248°–250°. The nmr spectrum was consistent with the assigned structure.

Analysis:
Calc'd for $C_6H_8N_4O_3S$: C 33.33; H 3.73; N 25.91;
Found: C 33.42; H 3.59; N 25.71.

The synthesis was repeated using 5.0 g of 5-amino-3-methyl-4-nitroisothiazole, 6.36 g of methyl isocyanate, and 1.18 ml of dibutyltin diacetate to give 5.3 g of solid which was recrystallized from tetrahydrofuran-hexane to give 3.0 g of light orange 1-methyl-3-(3-methyl-4-nitro-5-isothiazolyl)urea, m.p. 249°–251°.

The herbicidal activities of the compounds of this invention were demonstrated as follows. In preemergence tests, rows of seeds of lima beans (*Phaseolus lunatus*), corn (*Zea mays*), wild oats (*Avena fatua*), lettuce (*Lactuca sativa*), mustard (*Brassica juncea*) and crabgrass (*Digitaria sanguinalis*) were planted in shallow flat-bed trays (20 cm × 15 cm × 7.5 cm) containing 5 cm to 7.5 cm of sandy loam soil. Within 24 hours after planting, an aqueous acetone solution of the compound (using sufficient acetone to obtain solution) was sprayed on the soil at a rate equivalent to 8.96 kg/hectare, using a total volume equivalent to 760 liters per hectare. The trays were maintained under normal growing conditions in the greenhouse for about 3 weeks, after which the herbicidal efficacy of the compound was assessed. Individual plant specieswere examined in comparison with untreated plants.

In postemergence tests, rows of seeds were planted as for preemergence tests and the untreated flats were maintained in the greenhouse until the first trifoliate leaves of the bean plants were unfolding. The test plants were then sprayed with an aqueous acetone solution of the compound as for preemergence tests. The plants were returned to the greenhouse and held under normal growing conditions for about 3 more weeks, after which the herbicidal efficacy of the compound was assessed.

Table 1 lists data collected in the initial tests with 1-methyl-3-(3-methyl-4-nitro-5-isothiazolyl)urea. Table 2 lists data collected in the evaluation of that activity at reduced rates. It is seen that this compound is highly active, particularly in postemergence application, but is well tolerated by corn.

Table 1

Herbicidal Activity of
1-Methyl-3-(3-methyl-4-nitro-5-isothiazolyl)urea
(recorded as % kill at 8.96 kg/hectare)

|  | Preemergence | Postemergence |
| --- | --- | --- |
| Lima beans | 0 | 100 |
| Corn | 0 | 0 |
| Wild Oats | 80 | 0 |
| Lettuce | 90 | 100 |
| Mustard | 100 | 100 |
| Crabgrass | 90 | 100 |

Table 2

Herbicidal Activity of
1-Methyl-3-(3-methyl-4-nitro-5-isothiazolyl)urea
(recorded as % kill at indicated rate)

| | Rate (kg/hectare) | | | | |
| --- | --- | --- | --- | --- | --- |
| | 8.96 | 4.48 | 2.24 | 1.12 | 0.56 |
| Preemergence | | | | | |
| Lima beans | 100 | 80 | 80 | 0 | 0 |
| Corn | 0 | 0 | 0 | 0 | 0 |
| Wild Oats | 100 | 100 | 100 | 10 | 0 |
| Lettuce | 100 | 100 | 100 | 10 | 0 |
| Mustard | 100 | 100 | 100 | 0 | 0 |
| Crabgrass | 90 | 30 | 40 | 0 | 0 |
| Postemergence | | | | | |
| Lima beans | 100 | 100 | 100 | 0 | 0 |
| Corn | 0 | 0 | 0 | 0 | 0 |
| Wild Oats | 100 | 100 | 40 | 0 | 0 |
| Lettuce | 100 | 100 | 100 | 100 | 100 |
| Mustard | 100 | 100 | 100 | 100 | 100 |
| Crabgrass | 100 | 100 | 90 | 0 | 0 |

For herbicidal application, the compounds of this invention may be utilized in diverse formulations including the agricultural adjuvants and agricultural carriers, i.e. those materials normally employed to facilitate the dispersion of active ingredients in agricultural applications, recognizing the fact that the formulation and mode of application of a toxicant may effect the activity of the material in a given application. Thus, a compound of this invention may be formulated as a granule of relatively large particle size, as a wettable powder, as an emulsifiable concentrate, as a solution, or as any of several other known types of formulations, depending on the desired mode of application.

Granular formulations are particularly useful for aerial distribution or for penetration of a canopy of foliage. Useful granular formulations may be of several types. Impregnated granules are those wherein the active ingredient is applied to large particles of an absorbent carrier, such as an attapulgite or kaolin clay, corncobs, expanded mica, etc., normally in the form of a solution in a solvent. Surface-coated granules may be produced by spraying the molten active ingredient onto the surface of a generally nonabsorbent particle or by spraying on a solution of active ingredient in a solvent. The core may be water-soluble such as a prilled fertilizer, or insoluble such as sand, marble chips or coarse talc. Particularly useful is a granule wherein a wettable powder is applied as a surface coating to a sand or other insoluble particle such that the wettable powder may be dispersed on contact of the granule with moisture. Granules may be produced by agglomeration of dusts or powders by compaction rollers, by extrusion through a die or by use of a granulating disc. Granular formulations may vary widely in concentration, with useful formulations containing as little as 0.5% or as much as 95% of active ingredient.

Wettable powders, also useful formulations for both pre- and postemergence herbicides, are in the form of finely divided particles which disperse readily in water or other dispersants. The wettable powder is ultimately applied to the soil or to the undesired plant growth either as a finely divided dry material or as an emulsion in water or other liquid. Typical carriers for wettable powders include fuller's earth, kaolin clays, silicas and other highly absorbent, readily wet inorganic diluents. Wettable powders normally are prepared to contain about 5% to 80% of active ingredient, depending on the absorbency of the carrier, and usually also contain a small amount of a wetting, dispersing or emulsifying agent to facilitate dispersion. For example, a useful wettable powder formulation contains 80.8 parts of 1-methyl-3-(3-methyl-4-nitro-5-isothiazolyl)urea, 17.9 parts of palmetto clay, and 1.0 part of sodium lignosulfonate and 0.3 part of sulfonated aliphatic polyester as wetting agents.

Other useful formulations for herbicidal applications are the emulsifiable concentrates, which are homogeneous liquid or paste compositions dispersible in water or other dispersant, and may consist entirely of a compound of this invention with a liquid or solid emulsifying agent, or may also contain an agriculturally acceptable liquid carrier, such as xylene, heavy aromatic naphthas, isophorone and other nonvolatile organic solvents.

Typical wetting, dispersing or emulsifying agents used in agricultural formulations include, for example, the alkyl and alkylaryl sulfonates and sulfates and their sodium salts; polyethylene oxides; sulfonated oils, fatty acid esters of polyhydric alcohols; and other types of surface-active agents, many of which are available in commerce. The surface-active agent, when used, normally comprises from 1% to 15% by weight of the herbicidal composition.

These formulations may be applied without further dilution or as dilute solutions, emulsions or suspensions in water or other suitable diluent. The compositions may be applied to the area wherein control is desired by spraying onto the undesired vegetation or onto the surface of the soil in the case of liquid compositions or by distribution from mechanical equipment in the case of solids. The surface-applied material may also be blended into the upper layer of soil by cultivation, or left as applied, as is appropriate to gain the optimum results with the particular treatment.

The active herbicidal compounds of this invention may be formulated and/or applied with insecticides, fungicides, nematicides, plant-growth regulators, fertilizers, and other agricultural chemicals. In applying the active compounds of this invention, whether formulated alone or with other agricultural chemicals, an effective amount and concentration of isothiazolylurea are of course employed.

It is apparent that various modifications may be made in the formulation and application of the novel compounds of this invention, without departing from the inventive concept herein, as defined in the following claims:

I claim:

1. A substituted isothiazolylurea of the formula:

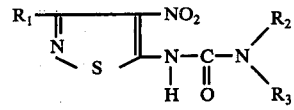

in which $R_1$ is straight or branched alkyl of 1 to 4 carbons; $R_2$ is alkyl of 1 to 4 carbons; $R_3$ is hydrogen or alkyl of 1 to 4 carbons.

2. The compound of claim 1 which is 1-methyl-3-(3-methyl-4-nitro-5-isothiazolyl)urea.

3. An herbicidal composition comprising an herbicidally effective amount of a compound of claim 1 in admixture with an agriculturally acceptable extender.

4. A method of preventing and destroying plant growth which comprises applying to the locus to be protected an herbicidally effective amount of a compound of claim 1.